United States Patent [19]

Vrieland et al.

[11] 4,075,122
[45] Feb. 21, 1978

[54] CATALYST AND METHOD OF OXYDEHYDROGENATION OF ALKYL AROMATIC COMPOUNDS

[75] Inventors: G. Edwin Vrieland, Midland, Mich.; Hans R. Friedli, Lake Jackson, Tex.

[73] Assignee: The Dow Chemical Company, Midland, Mich.

[21] Appl. No.: 618,730

[22] Filed: Oct. 1, 1975

Related U.S. Application Data

[62] Division of Ser. No. 474,124, May 28, 1974, Pat. No. 3,917,732.

[51] Int. Cl.$^2$ .............................................. B01J 27/16
[52] U.S. Cl. .................................................... 252/437
[58] Field of Search ......................................... 252/437

[56] References Cited

U.S. PATENT DOCUMENTS

| 2,456,367 | 12/1948 | Britton et al. | 252/437 |
| 3,935,126 | 1/1976 | Vrieland | 252/437 |

*Primary Examiner*—Winston A. Douglas
*Assistant Examiner*—Mark Bell
*Attorney, Agent, or Firm*—Glwynn R. Baker

[57] ABSTRACT

Magnesium nickel pyrophosphate is a superior catalyst for oxydehydrogenating alkyl aromatic compounds including nitrogen heterocyclics which have at least one $C_2$–$C_6$ alkyl side chain to form derivatives having side chain unsaturation. The alkyl aromatic compound can have 1–2 rings. The process is carried out at 450°–650° C. and a space velocity of 55–2500.

2 Claims, No Drawings

CATALYST AND METHOD OF OXYDEHYDROGENATION OF ALKYL AROMATIC COMPOUNDS

CROSS-REFERENCE TO RELATED APPLICATION

This application is a divisional of our copending Application Ser. No. 474,124 filed May 28, 1974 entitled METHOD OF OXYDEHYDROGENATION OF ALKYL AROMATIC COMPOUNDS, now U.S. Pat. No. 3,917,732 issued Nov. 4, 1975.

BACKGROUND OF THE INVENTION

Certain alkaline earth-nickel phosphates, such as calcium-nickel phosphate or strontium-nickel phosphate are good dehydrogenation catalysts for converting n-butenes to butadiene or for oxydehydrogenating lower aliphatic alkanes and alkenes to dienes. Although they also dehydrogenate alkyl aromatic hydrocarbons to their alkene aromatic derivatives, these catalysts are not as active for this purpose, as are the well-known self-regenerative catalysts containing iron, zinc or magnesium oxides and potassium oxide or a potassium compound convertible to the oxide.

One of the shortcomings of the self-regenerative dehydrogenation catalysts for converting ethylbenzene to styrene is that under acceptable commercially operating conditions the conversion of the ethylbenzene is in the 35–40% range. Selectivity, however, is in the 85–95% range. The self-regenerative catalysts are not sufficiently selective in oxydehydrogenation systems to be useful commercially for converting alkyl benzenes to alkene derivatives in the presence of oxygen.

Therefore, an object of this invention is the provision of a superior catalyst for oxydehydrogenation of an alkyl aromatic compound. Another object is to provide a process for oxydehydrogenating alkyl aromatic compounds in which process superior conversions with high selectivities of the alkyl group to an alkene group are obtained.

SUMMARY OF THE INVENTION

This invention concerns a novel catalyst and a method of oxydehydrogenating alkyl aromatic compounds having at least one $C_2$–$C_6$ alkyl group; including nitrogen heterocyclics, and 1–2 rings in the aromatic moiety, to form derivatives having aliphatic unsaturation in the side chain. More particularly, the catalyst is magnesium-nickel pyrophosphate which has been impregnated with phosphate ions. The catalyst can also contain small amounts of chromium oxide. The method comprises passing a mixture of an oxygen containing gas, and vapors of the alkyl aromatic compounds, with or without an inert diluent vapor, over the catalyst at a temperature of from about 450° C. to about 650° C., at a space velocity of from about 55 to about 2500.

DETAILED DESCRIPTION OF THE INVENTION

The novel magnesium-nickel pyrophosphate catalyst of this invention can contain from about 6 to about 9.5 atoms of Mg per atom of nickel.

The catalyst can be prepared by the general procedure described in U.S. Pat. No. 2,542,813 by commingling a mixture of $Ni(NO_3)_2$, $Mg(NO_3)_2$ and $H_3PO_4$ with water and $(NH_4)H_2PO_4$ or $(NH_4)_2HPO_4$ and $NH_3$ or it can be prepared by first preparing an aqueous solution of a water soluble nickel and magnesium salt and adjusting the pH to 6–7. This solution is added to a neutralized ammonium phosphate solution having a pH of about 7. The mixture is stirred rapidly during the addition and usually $NH_4OH$ is added slowly to maintain the pH no lower than 6, nor higher than about 7.

A specific method for making the catalyst is described below:

1. 69.3 g. $Mg(NO_3)_2 \cdot 6H_2O$ and 8.72 g. $Ni(NO_3)_2 \cdot 6H_2O$ was added to 250 cc water and the pH was adjusted to 6.5 with $NH_4OH$.
2. A solution of 44.6 g. $(NH_4)_2HPO_4$ in 250 cc water was neutralized to pH 7 with nitric acid.
3. Solution 1 was added to solution 2 with rapid stirring. Ammonium hydroxide was added slowly to maintain the pH at about 6.

The precipitate was filtered, dried and calcined at 550° C. to form a magnesium-nickel pyrophosphate in which the Mg to nickel mol ratio was about 9 to 1.

The molar ratio of oxygen to alkyl aromatic compound can range from about 0.5 to about 4.0 moles of $O_2$ per mol of alkyl aromatic compound, but a preferred range is from about 0.5 to about 1.5 and most preferred is a range of about 0.9 to about 1.1 mols $O_2$ per mol of aromatic compound.

The oxygen can be pure oxygen air or air enriched with oxygen.

The space velocity (vol./vol./hr.) can range from about 55 to 2500, but a preferred range is from about 250 to about 1800. Most preferred is a range of from about 800 to about 1800.

Diluents when used can be the noble gases, nitrogen, carbon dioxide or steam. These can range from about 4–16 volumes per volume of alkyl aromatic compound, but preferably range from about 4 to about 11 volumes.

The pressure at which the reaction can be run ranges from 0.5 to about 5 atmospheres, but it is preferable to operate at autogenous pressure which is generally the range of about 1 to about 2 atmospheres.

The reaction can be effected in a temperature range of from about 450° C. to about 650° C., but a preferred range is from about 500° C. to about 650° C.

Care should be exercised to avoid explosive mixtures when feeding the alkyl aromatic compound and oxygen into the reactor.

The examples which follow are intended to illustrate, but not to limit the invention. All parts are by weight unless specifically indicated otherwise.

The reactor for this example was a high silica glass tube 16 mm I.D. and 42 cm. long, with an inlet for the compound to be dehydrogenated and another for a premixed feed of oxygen and an inert diluent. After loading the reactor with catalyst, coarse, high silica chips were placed above the catalyst layer to serve as a mixing and preheating area. The reactor was heated by placing it in an electric resistance furnace.

The reactor was loaded with 20 ml. of the magnesium-nickel pyrophosphate catalyst, described above, and then high silica chips were loaded on top of the catalyst. The outlet from the reactor had a valved line connected to a vapor phase chromatograph, in which $O_2$, $N_2$, CO, $CO_2$ and benzene, toluene, alkyl aromatic and alkenyl aromatic hydrocarbon in the effluent were analyzed.

A mixture of 90 cc helium, 15 cc $O_2$ and 15 cc ethyl benzene (STP) per minute was fed to the reactor. The reaction temperature was 533° C. The conversion of ethyl benzene was 70.2% and the selectivity to styrene was 90.2% after 2½ hours of operation.

The GSHV of this example was about 360 hr.[-1]

We claim:

1. A catalyst for oxydehydrogenation of alkyl aromatic compounds consisting essentially of a magnesium pyrophosphate in which the ratio of magnesium to nickel is about 6 to about 9.5 atoms of magnesium per atom of nickel which has been calcined at about 550° C.

2. A magnesium nickel pyrophosphate in which the ratio of magnesium to nickel is about 9 to 1 and which has been calcined at about 550° C.

* * * * *

UNITED STATES PATENT AND TRADEMARK OFFICE
CERTIFICATE OF CORRECTION

PATENT NO. : 4,075,122
DATED : February 21, 1978
INVENTOR(S) : G. Edwin Vrieland; Hans R. Friedli It is certified that error appears in the above-identified patent and that said Letters Patent are hereby corrected as shown below:

Column 3, line 6, in Claim 1, add the word -- nickel -- at the beginning of the line.

Signed and Sealed this

Thirteenth Day of June 1978

[SEAL]

Attest:

RUTH C. MASON
*Attesting Officer*

DONALD W. BANNER
*Commissioner of Patents and Trademarks*